United States Patent [19]
Schöllner et al.

[11] Patent Number: 5,916,268
[45] Date of Patent: Jun. 29, 1999

[54] KIT FOR AN ARTIFICIAL ACETABULUM

[75] Inventors: Dietrich Schöllner, Rösrath-Forsbach, Germany; Yvan Sandoz, Winterthur, Switzerland

[73] Assignees: Sulzer Medizinaltechnik AG, Winterthur; Allo Pro AG, Baar, both of Switzerland

[21] Appl. No.: 08/009,204

[22] Filed: Jan. 25, 1993

[30] Foreign Application Priority Data

Jan. 29, 1992 [CH] Switzerland ............... 00249/92

[51] Int. Cl.⁶ ...................................... A61F 2/32
[52] U.S. Cl. ...................................... 623/22
[58] Field of Search .................. 623/16, 18, 22, 623/23

[56] References Cited

U.S. PATENT DOCUMENTS

| | | |
|---|---|---|
| 3,685,058 | 8/1972 | Tronzo . |
| 4,936,856 | 6/1990 | Keller ................................ 623/22 |

FOREIGN PATENT DOCUMENTS

| | | |
|---|---|---|
| 0 147 339 | 7/1985 | European Pat. Off. . |
| 0 169 975 | 2/1986 | European Pat. Off. . |
| 0 313 762 | 5/1989 | European Pat. Off. . |
| 0 314 951 | 5/1989 | European Pat. Off. . |
| 0 341 198 | 11/1989 | European Pat. Off. . |
| 0 341 199 | 11/1989 | European Pat. Off. . |
| 0 353 171 | 1/1990 | European Pat. Off. . |
| 90 16 523 U | 6/1991 | Germany . |
| WO 85/02535 | 6/1985 | WIPO . |
| WO88/01491 | 3/1988 | WIPO . |
| 0007845 | 10/1988 | WIPO ................................ 623/23 |

*Primary Examiner*—David J. Isabella
*Attorney, Agent, or Firm*—Townsend and Townsend and Crew LLP

[57] ABSTRACT

The kit contains a metal outer shell (1), an inner shell (2) which can be inserted therein, and fastening elements which can be mounted on the outer shell (1) so that they substantially protrude radially, and which include at least one support (4) and two screw connections (5). The fastening elements, which can be designed with varying support lengths, together with the outer shell (1) form a tripod, which positions the outer shell (1) outside the osseous tissue (6). The outer shell (1) is designed all around with through-holes (17) mounted at different angles (14), which permit the mounting of the screw connections (5) in correspondingly different angular positions with respect to the support (4). The kit, which by simple means enables an optimal adjustment of the acetabulum which can be corrected during implantation if necessary, is provided as a replacement for a missing pelvic part in the region of the hip joint

23 Claims, 3 Drawing Sheets

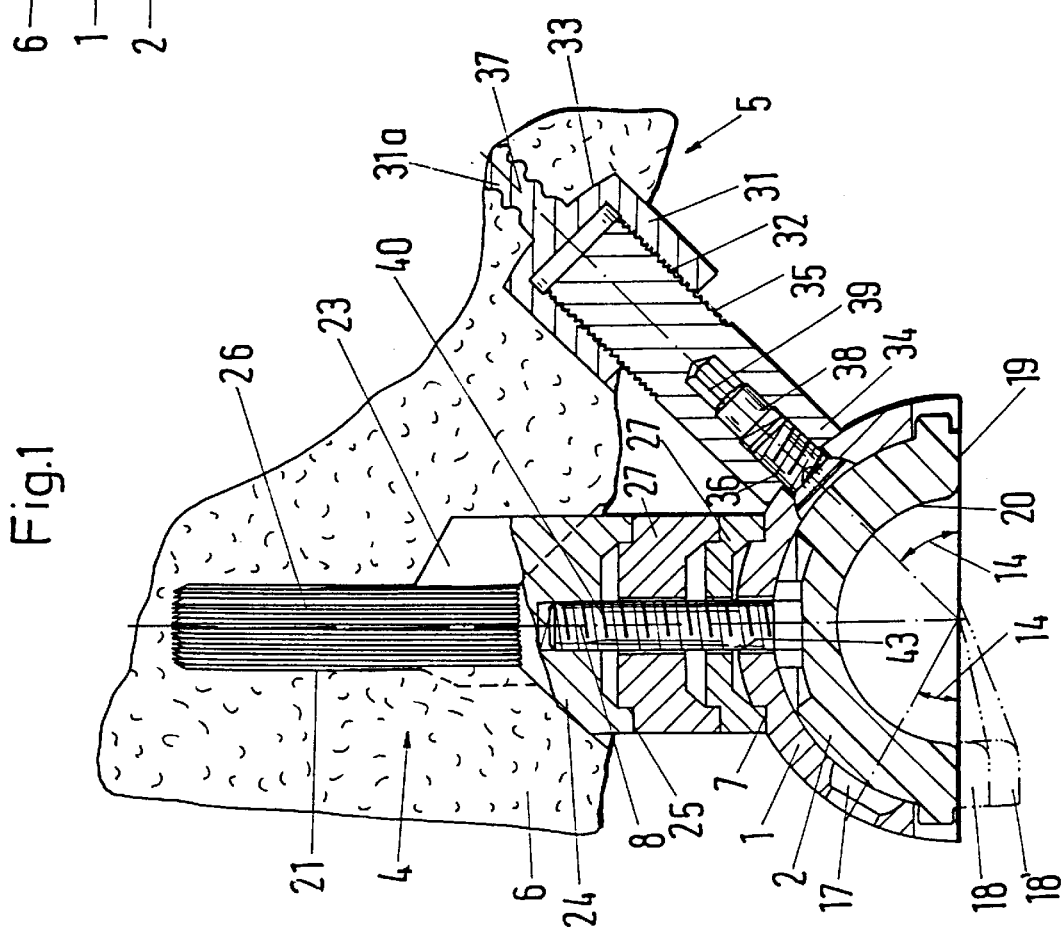

5,916,268

KIT FOR AN ARTIFICIAL ACETABULUM

BACKGROUND OF THE INVENTION

The invention relates to a kit for an artificial acetabulum made of a metal outer shell, an inner shell which can be inserted therein and fastening elements which are attached to the outer shell.

In a kit of the said type known from WO-A-88/01491 the outer shell is provided at two points on its circumference roughly opposite one another with tip-stretched lugs, each of which is constructed with a bore to receive a pin, which can be inserted therein with self-locking interference fit and which protrudes from a plate-shaped connecting piece which can be attached to a pelvic part. The known design is provided as a replacement for a missing pelvic part in the region of the hip joint, in which case plate-like retaining parts are to be screwed in the pubic bone-iliac bone region of the pelvis. The outer shell of the known kit provided with tip-stretched lugs produces a relatively voluminous component, the precise positioning of which in the region of the hip joint requires an individual adaptation of the shape of the connecting pieces to the anatomical conditions and/or a relatively complicated preparation of the parts of the pelvis to be constructed with relatively large dimensions for receiving these plate-shaped connecting pieces. Therefore the known kit can only be adapted to a limited degree to different anatomical conditions prevailing in the implantation region, which, in particular with respect to the dimensions of the pelvic part to be replaced and to the angular position of the parts to be implanted, in practice may vary within relatively wide limits. In order to guarantee permanent availability of such kits, which as a rule are relatively seldom used, it is therefore necessary to have a relatively large stock of such kits with several parts made in different sizes, in which case just one of the kits is selected according to the anatomical conditions prevailing, is adapted to these conditions and is finally implanted.

SUMMARY OF THE INVENTION

It is an object of the invention to create an improved kit of the aforementioned type which is as compact as possible and which has been simplified when compared with previous designs. It permits the use of components which can be easily produced and are easily adjustable, and which can be adapted substantially without additional machining to different anatomical conditions and can be positioned with respect to the region of the hip joint.

This object is achieved according to the invention in that the fastening elements comprise at least one support and two screw connections which, together with the outer shell, form a tripod that positions the outer shell outside the osseous tissue. It permits the selection of support lengths of different sizes between the outer shell and the osseous tissue for each fastening element.

The design according to the invention produces a kit in a compact style. The fastening elements can be adjusted substantially radially to the outer shell, to guarantee an improved, direct flux of force between the acetabulum and the regions of the pelvis receiving the fastening elements. Bores in the osseous tissue, which are relatively simple to make, assure a secure attachment of the three fastening elements of the kit by introducing one component of the supporting force —with a correspondingly low stress on the osseous tissue—into the respective pelvic part. The fastening elements, which can have different support lengths, provide an optimal and simple adjustment of the acetabulum which, if necessary, can be corrected during implantation.

BRIEF DESCRIPTION OF THE DRAWINGS

FIG. 1 is a sectional view which shows parts of the kit constructed according to the invention extending diametrally with respect to the outer shell;

FIG. 2 is a sectional view which shows further parts of the kit as shown in FIG. 1 in a radial partial section and staggered in the peripheral direction of the outer shell when compared with the representation in FIG. 1;

FIG. 3 is a sectional view similar to FIG. 2 which shows a detail of a kit as shown in FIG. 1 in a modified embodiment;

DETAILED DESCRIPTION OF THE PREFERRED EMBODIMENTS

Figure 5:
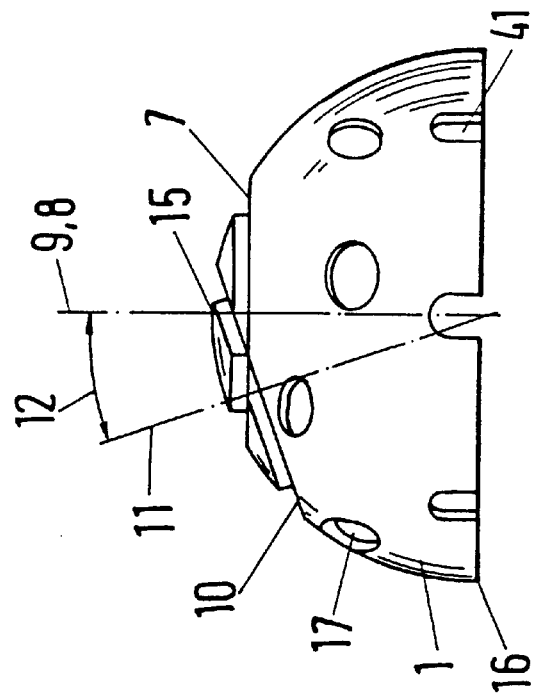
FIG. 5 is a side elevation which shows the part shown in FIG. 4.

The kit shown in FIGS. 1 and 2 contains a metal outer shell 1 in the shape of a hollow hemisphere, an inner shell 2, which can be inserted therein and which also has a hemispherical design, and fastening elements, which can be mounted on the outer shell 1 so that they protrude radially, in the form of a support 4 and two screw connections 5, which can be fixed in the osseous tissue 6 of a human pelvic part and by which the outer shell 1 can be positioned outside the osseous tissue 6. The kit is intended as a replacement for a missing pelvic part in the region of the hip joint.

Figure 4:
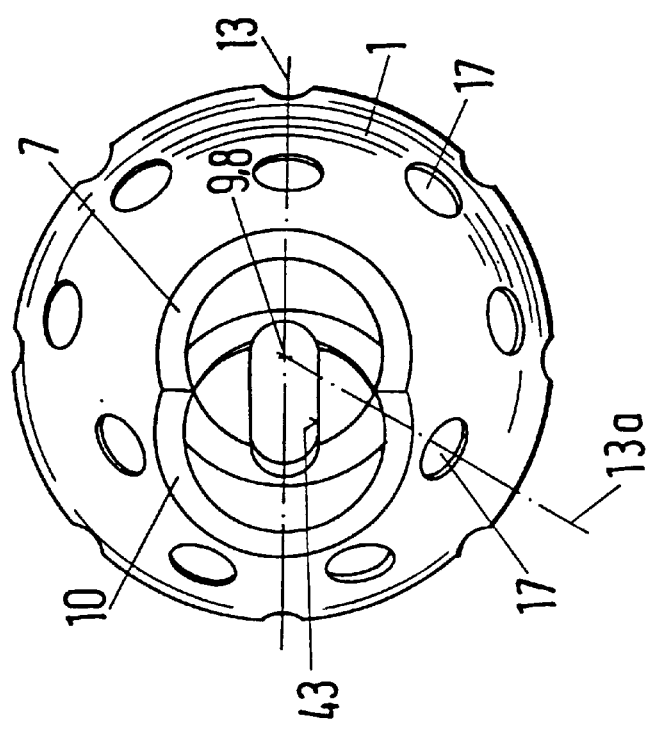
FIG. 4 is a plan view which shows a part of a kit of a modified embodiment.

The outer shell 1 has a bore 43 in the region of its pole 15 (FIG. 5) to receive a fastening screw 40 for the support 4. It also has a circular base 7 concentric to the bore 43 to support the support 4, which is disposed perpendicular to a centering axis 8 and coincides with the polar axis 9 of the outer shell 1. To receive the support 4 in a different angular position radially offset with respect to the polar axis 9, the outer shell 1 can be provided with at least one further base 10 which is inclined relative to and overlaps the base 7 as is shown in FIGS. 4 and 5. Base 10 is perpendicular to a second centering axis 11. The centering axis 11 encloses an angle 12 with centering axis 8 or the polar axis 9 respectively which lies in a plane of symmetry 13 on the outer shell 1 as shown. As can be seen from FIG. 4, with this design the bore 43 is constructed as a slot, which permits appropriate adjustments of the fastening screw 40 concentric to one of the bases 7 or 10. Further, appropriately inclined bases 10 may also be provided. The angle 12 can be freely selected within the limits imposed by the dimensions of the outer shell 1 and of the support 4. The design shown, in which the angle 12 may be up to 20°, permits an optimal adaptation to most prevailing anatomical conditions.

Between its pole 15 and its equator 16 the outer shell 1 is also provided with several radial through-holes 17. They are staggered in the circumferential direction and their axes 37 are inclined to the plane of the equator 16 at various angles 14. Each of the through-holes 17 is intended to receive a fastening screw 36 for one of the screw connections 5 to be mounted on the outer shell 1 in correspondingly different positions (FIGS. 1, 2) or to receive a bone screw 29 which can be attached directly in the pelvic region (FIG. 3). It is expedient if the through-holes 17, as shown in FIG. 4, are symmetrically disposed on the outer shell 1 with respect to the plane of symmetry 13 so that it can be used both for the right-hand and the left-hand hip joint region.

In the region of the equator 16 the outer shell 1 can be constructed with several recesses 41 distributed over the circumference, which are intended to receive cams 42 provided on the inner shell 2. Eight such recesses are shown. The inner shell 2, which may also be made of metal, or, as shown in the drawings, of a plastic, can be interlocked with the outer shell 1 via the cams 42 in various angular positions around the polar axis 9. In this case the inner shell 2 can be constructed with a raised part 18 or 18' on one side shown by dot-dash lines in FIG. 1, which protrudes by a predetermined amount over the edge 19 of the outer shell 1 to provide a sufficiently secure guidance of the condyle to be received by the inner hemispherical surface 20 even under unfavorable anatomical conditions in the hip joint region, which, for example, restrict the positioning of the acetabulum to one functionally unfavorable angular position.

The support 4 contains a cylindrical or conical attachment part 21, which can be fixed in the osseous tissue 6, having a collar part 24 which conically widens in the outward direction, two cylindrical spacers 27 and the attachment screw 40 for bracing the outer shell 1 via the spacers 27 against the collar part 24. The attachment part 21 is designed with a structured surface 22, which as shown may have small cutting edges 26 which extend longitudinally along the surface lines of the cylindrical attachment part 21 parallel to the centering axis 8. The attachment part 21 and the collar part 24 are also connected to one another by at least one radially positioned longitudinal fin 23, or as shown two corresponding longitudinal fins, which can both be introduced into a slit to be provided in the osseous tissue 6, to prevent the attachment part 21 from rotating. The collar part 24 and the spacers 27 are each constructed with a collar surface 25 complementary to the base 7 or 10 of the outer shell 1, each of the spacers 27 being provided with a supporting surface corresponding to the base 7 or 10 respectively. A stock of several spacers 27 of varying thicknesses is preferably provided so that spacers can be appropriately combined to vary the overall length of the support in relatively fine graduation for a precise positioning of the outer shell 1 in the direction of the centering axis 8.

The screw connection 5 shown in FIG. 1, which can be mounted on any through-hole 17 on the outer shell 1, and shown in the plane of symmetry 13, contains a sleeve 31 which can be screwed into the osseous tissue 6. The sleeve further includes an internal screw thread 32 which engages a corresponding external screw thread 35 on an adapter 34 which can thus be moved to adjust its position in the direction of the axis 37 of the respective through-hole 17. The adaptor 34 is connected to the outer shell 1 via a detachable screw connection formed by a fastening screw 36 which can be screwed from the inside of the outer shell 1 into the adaptor 34 and which may be provided with a hexagon socket as shown. The internal cavity 38 is constructed with contact surfaces 39, which are shown in the form of a hexagon socket, to receive a socket spanner which can be introduced through the through-hole 27, by which—when the fastening screw 36 is unscrewed—the adaptor 34 can be adjusted with respect to the axis 37 in any angle of rotation, as a result of which a corresponding depth adjustment of the adaptor 34 in the sleeve 31 can be achieved. As shown in FIG. 1 the sleeve 31 can be provided with a tip-stretched, bone screw 31a protruding from its front end 33 for pressing the front 33 against a corresponding supporting surface of a recess in the osseous tissue receiving the sleeve.

A second screw attachment 5 of the kit shown in FIG. 1, which is mounted on the outer shell 1 so that it is offset in the circumferential direction relative to the first screw attachment 5 described above, e.g. in a radial plane 13a shown in phantom lines in FIG. 4, can be constructed as was described above or as shown in FIG. 2. With the screw attachment 5 shown in FIG. 2, which only differs slightly from the one shown in FIG. 1, the adaptor 34 is provided with an axial bore connected to the internal cavity 38, as a result of which the weight of the adaptor 34 is accordingly reduced, and the sleeve 31 is provided with a bore on the front end to receive a removable bone screw 39 which can be screwed into the osseous tissue 6 for pressing the front surface 33 of the sleeve 31 against the osseous tissue 6. It is obvious that a screw connection 5 as shown in FIG. 2 may be used instead of the screw connection 5 shown in FIG. 1.

According to the prevailing anatomical conditions, in particular with a relatively small distance between the outer shell 1 and the adjacent pelvic region, at least one of the two screw connections 5 can be formed by a simple screw connection 28 as is shown in FIG. 3. It has at least one spacer disc 30 of appropriate thickness which can be mounted between the osseous tissue 6 and the outer shell 1, and one bone screw 29 which can be screwed into the osseous tissue 6 from the inside of the outer shell 1 through the appropriate through-hole 17 and a corresponding bore in the spacer disc 30.

It is expedient to stock several spacer discs 30 of various thicknesses and several adaptors 34 which, if necessary, are made in various lengths. This provides fast access to parts which are sized to fit the prevailing anatomic conditions, or which can be combined with one another if necessary.

Figure 6:
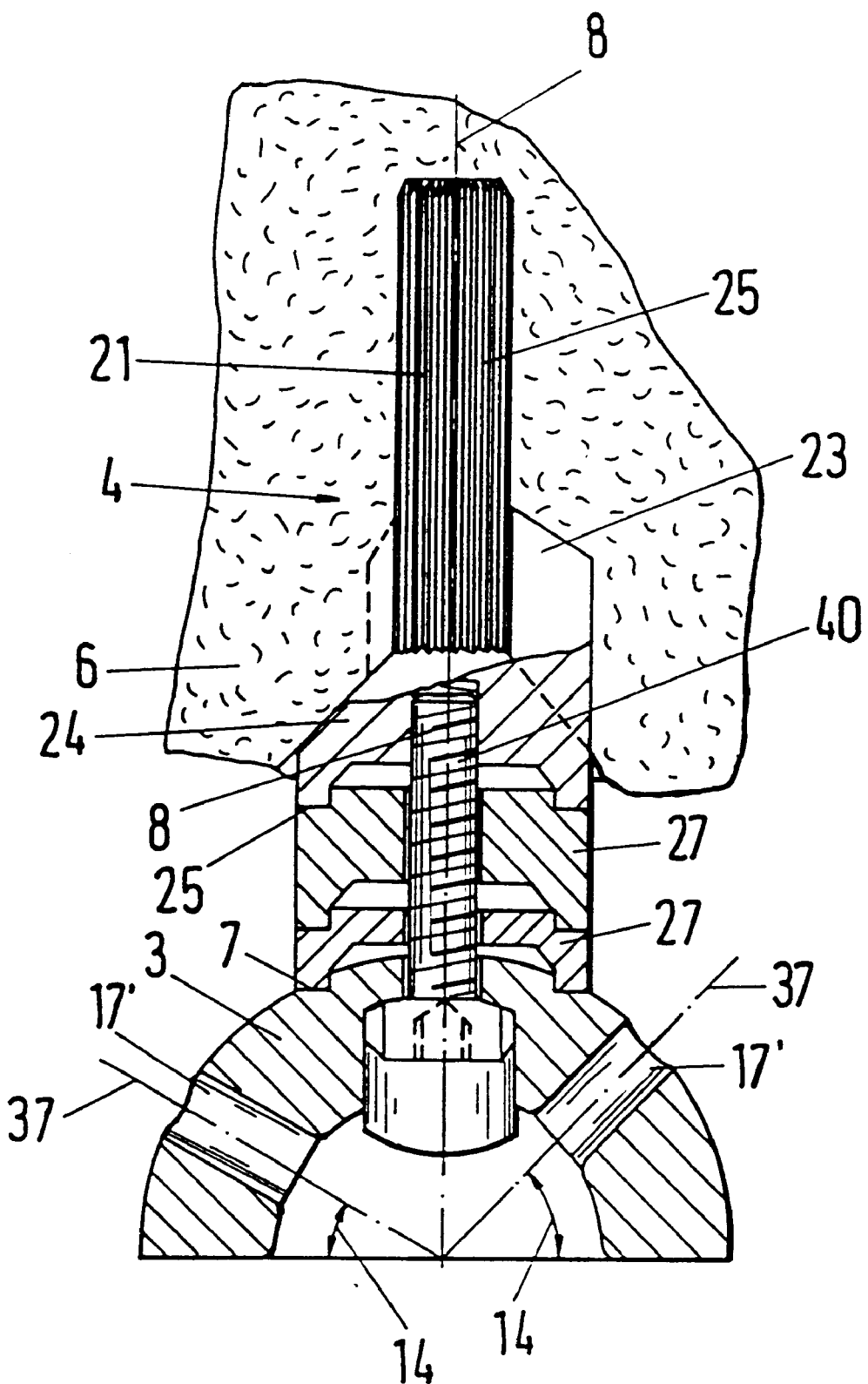
FIG. 6 is a sectional view which shows parts of the kit as shown in FIG. 1 with an auxiliary device for the preparation of parts of the osseous tissue intended to receive the other parts of the kit.

To prepare the implantation of the artificial acetabulum, recesses are cut into the osseous tissue 6 which correspond to the center of the support 4—a bore corresponding to the attachment part 21 and the collar part 24 and slits corresponding to the longitudinal fins 23. The support 4 is forced into these recesses. As shown in FIG. 6, in a next step a hole gauge 3 is attached to the support 4 via appropriate spacers 27 with fastening screw 40. The hole gauge 3 corresponds in its mating dimensions to the outer shell 1 to be subsequently mounted in its final position.

The hole gauge 3 also has the form of a hollow hemisphere and includes through-holes 17' to guide a boring mill. Holes 17' are positioned to correspond to through-holes 17 in the outer shell 1 to be implanted. As can also be seen from FIG. 6, the hole gauge 3 can have a substantially greater wall thickness than the outer shell 1 to assure a good guidance of the boring mill by the through-holes 17'. For forming the screw connections 5 provided as an additional support, the hole gauge 3, which can rotate around the centering axis 8, can be fixed in a position in which two appropriate through-holes 17' are oriented towards the pelvic parts. The bores for the bone screws 29 and 31a and the contact surfaces for the front end 33 of the spacer discs 30 and/or of the sleeves 31 are cut into the osseous tissue 6 with the boring mill, which can be introduced through holes 17'.

When unfavorable anatomical conditions are encountered which do not allow a second screw connection, e.g. because of the lack of a suitable bone part, an adequate attachment of the acetabulum may be attained with a single screw connection 5, in conjunction with the support 4. It is obvious that a third screw connection 5 may also be provided if the need arises.

After the bores have been made in the osseous tissue 6 the hole gauge 3 is removed from the support 4. A sleeve 31 of the adjustable screw connection can now be fixed by means of a bone screw 29 or 31a extending into the osseous tissue 6 and one of the adaptors 34 can be screwed into the sleeves 31. If the anatomical conditions permit, a simple screw connection 28 as shown in FIG. 3, which does not contain a sleeve 31, can be used instead of at least one of the adjustable screw connections 5. Next, the outer shell 1 is connected in its desired position to the support 4 via the spacers 27, and when using a simple screw connection 28 an appropriate spacer disc 30 is inserted between the contact surface of the osseous tissue 6 and the outer shell 11, via which the outer shell 1 is braced by means of the bone screw 29 against the osseous tissue 6. In a further process step the adaptor 34 is screwed out of the respective sleeve 31 with a socket spanner until it abuts flush against the outer shell 1 and it is then rigidly screwed to the outer shell 1. Finally the inner shell 2 is inserted into the outer shell 1 and is secured thereto by engaging cams 42 with the recesses 41. In the case of inner shells 2 with a raised edge 19 on one side attention has to be paid to the appropriate angular position of the raised part 18, 18'.

What is claimed is:

1. A kit for an artificial acetabulum comprising:

a metal outer shell having an outer surface and an inner surface;

an inner shell for insertion into the outer shell and against the inner surface thereof;

connecting means projecting from the outer surface of the outer shell for securing the outer shell to a bone structure and including at least one support adapted to be immovably anchored to the bone structure, at least two screw connections adapted to be screwed into the bone structure, and means for releasably securing the outer shell to the support and to the screw connections; and adjustment means operatively coupled with the connecting means for locating the outer shell at a desired position which is spaced from the bone structure.

2. A kit according to claim 1 wherein the outer shell comprises a hemispherically shaped shell defining a polar axis.

3. A kit according to claim 2 including a base formed on the outer surface of the outer shell for receiving the support, the base being concentric with the polar axis of the outer shell.

4. A kit according to claim 3 including at least one additional base on the outer surface of the shell for receiving the support and having an axis which is angularly inclined relative to the polar axis by up to 20°, the axis of the additional base and the polar axis defining a plane of symmetry for the outer shell.

5. A kit according to claim 2 wherein the shell terminates in a generally circular end face substantially concentrically disposed relative to the polar axis, and including a plurality of through-holes in the outer shell arranged between the polar axis and the end face and adapted to receive the screw connections, whereby the orientations of the screw connections relative to the polar axis can be selected by selecting appropriately located through-holes for them.

6. A kit according to claim 5 wherein the outer shell includes a plane of symmetry extending through the polar axis, and wherein the through-holes are distributed symmetrically relative to the plane of symmetry over the outer shell.

7. A kit according to claim 2 wherein the outer shell and the inner shell include attachment means for substantially immovably attaching the inner shell to the outer shell at a plurality of selectable positions which are angularly offset about the polar axis.

8. A kit according to claim 7 wherein the angular offset of the selectable positions of the inner shell is a rotational offset of the inner shell relative to the outer shell with the polar axis defining an axis of rotation for the offset.

9. A kit according to claim 7 wherein the inner shell includes a raised portion projecting past an end face defined by the outer shell when the inner shell is inserted in the outer shell.

10. A kit according to claim 2 wherein the outer shell defines on the outer surface a first base which is concentric about the polar axis and a second base which is concentric about a second axis which is angularly inclined relative to the polar axis, the bases being of like shape, and wherein the support includes an attachment part having a generally circular cross-section and a structured outer surface, a relatively enlarged collar projecting from an end of the attachment part towards the outer shell and defining a collar surface shaped complementary to the bases so that the collar surface can be supported on the bases, and a longitudinal fin connecting the attachment part to the collar and projecting generally radially away therefrom, whereby the attachment part can be secured to one of the bases on the outer surface of the outer shell at any desired relative angle of rotation about the axes of the bases.

11. A kit according to claim 10 wherein the attachment part has a cylindrical shape.

12. A kit according to claim 10 wherein the attachment part has a conical shape.

13. A kit according to claim 10 wherein the structured surface defines longitudinally extending cutting edges on its exterior which are adapted to become embedded in the bone structure when the attachment part is forced into the bone structure.

14. A kit according to claim 10 including spacers disposed between the collar and the base on the outer shell to which the collar is to be connected, each spacer including an end surface shaped to engage the base and an opposing end surface shaped to engage the collar.

15. A kit according to claim 5 wherein at least one of the screw connections comprises a bone screw engaging the outer shell, extending through one of the through-holes and adapted to be screwed directly into the bone structure, and a spacer disc adapted to be placed between the outer shell and the bone structure and abutting the outer shell.

16. A kit according to claim 15 including a plurality of spacer discs of varying thicknesses, whereby, during the implantation of the outer shell, a disc can be selected which has a thickness so that the disc abuts the outer shell and the bone structure into which the bone screw extends.

17. A kit according to claim 5 wherein at least one of the screw connections comprises an at least partially tubular sleeve having a first end adapted to be screwed directly into the bone structure, a second, open end, and an internal thread terminating at the open end, an adaptor extending through the open end into the sleeve and threadably engaging the internal thread thereof, whereby rotation of the adaptor relative to the sleeve causes them to move axially with respect to each other, and means extending through a selected through-hole and accessible from the inside surface of the outer shell for fixedly securing the adaptor to the outer shell at any rotational position of the adaptor with respect to the sleeve so that the outer shell can be fixed at the desired position.

18. A kit according to claim 17 wherein the adaptor includes a cavity extending into the adaptor from an end thereof proximate the selected through-hole and defining contact surfaces adapted to be engaged for rotating the adaptor relative to the sleeve when the means for fixedly securing is removed so that the contact surfaces are accessible through the selected through-hole.

19. A method for attaching an artificial acetabulum to a bone structure in spaced-apart relation thereto, the method comprising the steps of:

provided an artificial acetabulum including a generally semispherically shaped outer shell having a plurality of through-holes arranged at desired locations between an end face and a polar axis of the outer shell, and an inner shell for insertion into and attachment to the outer shell;

forming an opening in the bone structure;

anchoring a support for the artificial acetabulum in the opening;

providing a hole gauge having the same shape as the outer shell and securing the hole gauge to the support so that the hole gauge is in a position relative to the bone structure where the outer shell is to be located;

forming first and second holes with the hole gauge in the bone structure which are aligned with first and second through-holes in the outer shell selected to be used for attaching the outer shell to the bone structure;

removing the hole gauge from the support;

providing a sleeve having a first end defining a bone screw, a second, open end and an internal thread extending from the open end into the sleeve and screwing the sleeve into a selected one of the formed holes;

threadably attaching an elongated adaptor to the sleeve so that a proximal end of the adaptor extends past the open end of the sleeve;

securing the outer shell in its desired position to the support;

placing a spacer disc concentrically to the other one of the selected through-holes between the bone structure and the outer shell and applying a bone screw through the other one of the selected through-holes and the spacer disc into the second hole formed in the bone structure;

turning the adaptor relative to the sleeve until the proximate end of the adaptor abuts the outer shell;

fixedly securing the outer shell to the adaptor; and inserting the inner shell in and attaching it to the outer shell.

20. A method according to claim 19 wherein the proximate end of the adaptor includes a threaded bore and a socket defined by angularly inclined surfaces, wherein the step of turning the adaptor comprises extending a wrench through the through-hole aligned with the adaptor, with the wrench engaging the socket, and turning the wrench to thereby turn the adaptor, and wherein the step of securing the shell to the adaptor comprises the step of threadably engaging the threaded bore in the adaptor with a screw extending through the through-hole aligned with the adaptor.

21. A method according to claim 19 wherein the step of attaching the outer shell to the support includes the step of placing at least one spacer between an end of the support and the outer shell.

22. A method according to claim 19 wherein the step of placing a spacer disc includes the step of determining a distance between the outer shell and the bone structure along the axis of the selected through-hole and selecting a spacer disc having a thickness equal to the distance.

23. A method according to claim 19 wherein the inner shell includes a raised portion which extends past the end face of the outer shell when the inner shell is inserted in the outer shell, and including the step of turning the inner shell relative to the outer shell until the raised portion is at a desired position relative to the outer shell, and thereafter performing the step of attaching the outer shell in the inner shell.

* * * * *